United States Patent
Smith (10) Patent No.: US 9,381,028 B2
(45) Date of Patent: Jul. 5, 2016

(54) INVERSIBLE TUBULAR MEMBER AND A GRIPPING DEVICE INCLUDING SUCH A MEMBER

(75) Inventor: James Smith, Knysna (ZA)

(73) Assignee: Endogrowth (Proprietary) Limited, Wittedrif (ZA)

( * ) Notice: Subject to any disclaimer, the term of this patent is extended or adjusted under 35 U.S.C. 154(b) by 404 days.

(21) Appl. No.: 13/876,164

(22) PCT Filed: Oct. 13, 2011

(86) PCT No.: PCT/IB2011/054535
§ 371 (c)(1),
(2), (4) Date: Mar. 26, 2013

(87) PCT Pub. No.: WO2012/049652
PCT Pub. Date: Apr. 19, 2012

(65) Prior Publication Data
US 2013/0226196 A1    Aug. 29, 2013

(30) Foreign Application Priority Data
Oct. 15, 2010 (ZA) ................. 2010/07398

(51) Int. Cl.
*A61B 17/221* (2006.01)
*A61B 17/22* (2006.01)
*A61B 17/00* (2006.01)

(52) U.S. Cl.
CPC ......... *A61B 17/22031* (2013.01); *A61B 17/221* (2013.01); *A61B 2017/00287* (2013.01); *A61B 2017/00867* (2013.01); *A61B 2017/2215* (2013.01); *A61B 2017/22035* (2013.01)

(58) Field of Classification Search
CPC .................. A61B 17/22031; A61B 17/22032; A61B 17/221; A61B 17/32056; A61B 17/320716; A61B 2017/2212; A61B 2017/2215; A61B 2017/2217; A61B 2017/22035; A61B 2017/00287; A61B 2017/22034; A61B 2017/3435; A61B 17/22; A61B 17/3207; A61B 17/320708; A61B 17/320725; A61B 17/32075; A61B 2017/22037; A61B 2017/3443; A61B 2017/3433; A61B 2017/3207; A61B 2017/320716; A61B 2017/320733; A61B 2017/320741; A61B 10/02; A61B 10/04; A61B 2010/0208; A61B 1/00151; A61M 25/0119; A61F 2/013; A61F 2002/011
USPC ......................................... 606/127, 114, 200
See application file for complete search history.

(56) References Cited

U.S. PATENT DOCUMENTS

| 5,171,305 A * | 12/1992 | Schickling | A61M 25/0119 604/271 |
| 2004/0153117 A1 * | 8/2004 | Clubb | A61F 2/01 606/200 |

(Continued)

FOREIGN PATENT DOCUMENTS

WO    WO 2009/086482    7/2009

OTHER PUBLICATIONS

PCT International Search Report dated Mar. 20, 2012 in International Application No. PCT/IB2011/054535 filed on Oct. 13, 2011.

(Continued)

*Primary Examiner* — Darwin Erezo
*Assistant Examiner* — Katherine Schwiker
(74) *Attorney, Agent, or Firm* — Knobbe, Martens, Olson & Bear, LLP (57) ABSTRACT

This invention relates to a gripping device (10), e.g. a surgical retrieval device. The device includes an inversible tubular member (28), which is composed of interengaged stitches of resiliently flexible filamentary material and which is progressively transformable between an everted condition and an inverted condition. The device includes also actuation means (12,20) carrying the inversible tubular member and operable for effecting progressive inversion and eversion of the inversible tubular member. Through progressive inversion of the inversible tubular member, an object can be gripped thereby.

13 Claims, 7 Drawing Sheets

(56) References Cited

U.S. PATENT DOCUMENTS

| | | | |
|---|---|---|---|
| 2005/0055047 A1* | 3/2005 | Greenhalgh | A61F 2/01 606/200 |
| 2010/0087854 A1* | 4/2010 | Stopek | A61B 17/0057 606/215 |
| 2010/0137846 A1 | 6/2010 | Desai et al. | |
| 2010/0249815 A1 | 9/2010 | Jantzen et al. | |

OTHER PUBLICATIONS

PCT International Preliminary Report on Patentability dated Jan. 28, 2013 in International Application No. PCT/IB2011/054535 filed on Oct. 13, 2011.

* cited by examiner

INVERSIBLE TUBULAR MEMBER AND A GRIPPING DEVICE INCLUDING SUCH A MEMBER

THIS INVENTION relates to an inversible tubular member and to a gripping device including such a member.

According to a first aspect of the invention there is provided an inversible tubular member which is substantially round in cross-section and progressively transformable between an everted condition and an inverted condition, with a transformation end being defined intermediate an everted length and an inverted length of the inversible tubular member during such transformation and with the inverted length and the everted length defining opposite to the transformation end respectively an inverted end and an everted end of the inversible tubular member, in which:

the inversible tubular member is composed of interengaged stitches of resiliently flexible filamentary material;

with the inversible tubular member at least partially inverted, the inverted length has sufficient stiffness to cause eversion of the inversible tubular member at the transformation end upon axial displacement of the inverted end towards the transformation end, for a length of the inverted length up to X times an average relaxed outer diameter of the inverted length;

$X >= 2.0$;

with the inversible tubular member at least partially everted, the everted length has sufficient stiffness to cause inversion of the inversible tubular member at the transformation end upon axial displacement of the everted end towards the transformation end, for a length of the everted length up to Y times an average relaxed outer diameter of the inverted length; and $Y >= 2.0$.

In a particular embodiment of the inversible tubular member of the invention:

with the inversible tubular member at least partially everted, the everted length has sufficient stiffness to cause inversion of the inversible tubular member at the transformation end upon axial displacement of the everted end towards the transformation end, for a length of the everted length up to Z times the average relaxed outer diameter of the inverted length, whilst one half of a sphere of diameter 1.5 times an average relaxed outer diameter of the inverted length is received in the inversible tubular member at the transformation end; and $Z >= 2.0$.

The applicant has found that, by suitable selection of the filamentary material, pattern of the stitches, and so forth, the following values are achievable:

$X >= 5.0$ with the inverted length not restrained against lateral buckling;

$X >= 30$ with the inverted length restrained against lateral buckling, for example by the everted length;

$Y >= 50$; and $Z >= 3.0$.

In a particular embodiment of the inversible tubular member, it may define in the everted condition a larger outer diameter than in the inverted condition. Preferably, the inner diameter of the inversible tubular member in the everted condition is larger than its outer diameter in the inverted condition. As a result, during inversion and eversion, friction between an inverted length and an everted length of the inversible tubular member will be minimized.

The stitches may be knitted stitches of at least one length of the filamentary material.

The stitches may be plaited stitches, each defining a loop.

The filamentary material may be a monofilament material, for example a polymer such as Nylon. Alternatively, the filamentary material may be a multifilament material, for example stranded stainless steel wiring.

The filamentary material may be a superelastic material.

The filamentary material may be a shape memory material, e.g. Nitinol.

The inversible tubular member may have a substantially constant cross-section along its length in each of the inverted and everted conditions.

Alternatively, the inversible tubular member may have a variable diameter along its length in each of the inverted and everted conditions. Such a variable diameter may be achieved by varying the stitch size, or the number of stitches per circumferential row, along the length. Alternatively, if the properties of the filamentary material permit, a variable diameter may be achieved by heating, setting, and cooling of the filamentary material. The Applicant believes that such variable diameter may be useful in at least one envisaged application of the inversible tubular member, i.e. grabbing of an object, as is described below.

The filamentary material may be coated in a coating of a different material. The coating may, for example, serve to alter at least one surface property of the filamentary material, for example its coefficient of friction. In the case of the filamentary material being a multifilament material, the coating may serve to bind the filaments of the multifilament material together.

According to a second aspect of the invention there is provided a gripping device including:

an inversible tubular member which is substantially round in cross-section and progressively transformable between an everted condition and an inverted condition, with a transformation end being defined intermediate an everted length and an inverted length of the inversible tubular member during such transformation and with the inverted length and the everted length defining opposite to the transformation end respectively an inverted end and an everted end of the inversible tubular member, the inversible tubular member being composed of interengaged stitches of resiliently flexible filamentary material; and actuation means carrying the inversible tubular member and operable for effecting progressive inversion and eversion of the inversible tubular member, the inversible tubular member defining a transformation end where the progressive inversion and eversion occurs, with such inversion providing for gripping an object in the inversible tubular member.

The gripping device may be used for gripping an object, as is described below. The inversible tubular member must have rigidity sufficient for performing the method.

In the gripping device, the inversible tubular member may be an inversible tubular member, in accordance with the first aspect of the invention. Accordingly, further features of the inversible tubular member of the gripping device may be the same as any of the features of the inversible tubular member of the first aspect of the invention, as described above. Also, it is envisaged that the following relationship may apply in the inversible tubular member, where X and Y are as defined above:

$$X>=Y>=5.0$$

The applicant envisages that the gripping device of the second aspect of the invention may be used for the retrieval of loose objects from small or deep cavities where other forms of access may be difficult or impossible. It may also be used for gripping objects while they are being manipulated, modified, inspected, dissected, or excised. Typical applications could include capture and manipulation/removal of objects/organs during laparoscopic surgery, capture and removal of objects from natural body orifices, and capture and manipulation/removal of objects in/from pipes or machinery.

The gripping device may include a membrane over at least a part of a surface of the inversible tubular member which is an outer surface in the everted condition. Alternatively or additionally, the gripping device may include a membrane over at least a part of a surface of the inversible tubular member which is an inner surface in the everted condition.

In a particular embodiment of the gripping device, the actuation means includes:
  an outer tubular member defining a distal end, i.e. a front end, and a proximal end, i.e. a rear end, and a longitudinal passage extending between the distal end and the proximal end, the distal end being peripherally attached to an everted end of the inversible tubular member; and
  an inner elongate member received within the passage and defining a distal end and a proximal end, the distal end being peripherally attached to an opposite inverted end of the inversible tubular member,
the outer tubular member and the inner elongate member being slidingly displaceable relative to each other to effect the progressive inversion and eversion.

In the said particular embodiment, the actuation means may include:
  a first hand grip formation on the proximal end of the outer tubular member; and
  a second hand grip formation on the proximal end of the inner elongate member, the hand grip formations being manually relatively displaceable for effecting the relative sliding displacement of these members.

Still in the said particular embodiment, the inversible tubular member may be retractable into the outer tubular member.

Still in the said particular embodiment, the inner elongate member may be received within the outer tubular member in a snug sliding fit to provide sealing between these members to a required pressure, which is not less than 15 mmHg. Such sealing may be required in certain medical applications of the gripping device, as envisaged by the applicant.

Alternatively, the said particular embodiment may include sealing means, for example a circular sealing ring, sealing between the inner elongate member and the outer tubular member to a required pressure, which is not less than 15 mmHg.

Still in the said particular embodiment, the inner elongate member may define therethrough a longitudinal passage, permitting insertion of an elongate surgical or other instrument through it. This may be required in certain medical applications, for example laparoscopic applications, of the gripping device, as envisaged by the applicant. The inner elongate member may have sealing means sealing the longitudinal passage defined therethrough, the sealing means being configured to permit passage of an elongate surgical or other instrument through it and to seal around the instrument. The sealing means may, for example, include a duckbill for sealing the longitudinal passage when there is no instrument in the passage and a circular seal for sealing around an instrument when present in the passage.

Still in the said particular embodiment, the inversible tubular member may be releasable from the outer tubular member and the inner elongate member. In this case, the gripping device may include a first coupling secured to the everted end of the inversible tubular member, the first coupling being releasably engageable with the distal end of the outer tubular member; and a second coupling secured to an end of an inverted length of the inversible tubular member opposite to the transformation end, the second coupling being releasably engageable with the distal end of the inner tubular member. The first and second couplings may be interengageable through relative displacement of the outer tubular member and the inner elongate member.

Still in the said particular embodiment, the outer tubular member may include a distal end portion that is radially expandable for operatively accommodating therein a length of the inversible tubular member and an object therein where the size of the object requires radial expansion of the end portion. The distal end portion may define therein an arrangement of slits which are angularly spaced about the central axis of the tubular member to provide for the expansion. The distal end portion may be resiliently flexible to provide for the expansion.

According to a third aspect of the invention, there is provided a method of gripping an object, the method including:
  providing an inversible tubular member which is substantially round in cross-section and progressively transformable between an everted condition and an inverted condition with a transformation end being defined intermediate an everted length and an inverted length of the inversible tubular member during such transformation, the inversible tubular member being composed of interengaged stitches of resiliently flexible filamentary material;
  with at least a part of the length of the inversible tubular member in the everted condition, contacting the transformation end of the said part with the object; and
  progressively inverting the said part at the transformation end, thus causing the inversible tubular member to grip the object.

Clearly, in order to perform the method, the inversible tubular member must have sufficient rigidity.

The inversible tubular member used in the method may be an inversible tubular member, in accordance with the first aspect of the invention.

The method may include at least partially drawing the object into the inversible tubular member by the progressive inverting of the inversible tubular member.

The applicant has found that, due to flexibility in the inversible tubular member, the method may be used to grip and draw into the inversible tubular member an object having a size substantially larger than the outer diameter of the said part of the length of the inversible tubular member in the everted condition. The applicant has further found that, by suitably sizing the inversible tubular member, it is able to grip and draw in very fragile objects.

According to a fourth aspect of the invention there is provided a method of making an inversible tubular member, in accordance with the first aspect of the invention, the method including forming stitches in a suitable filamentary material and inter-engaging them to define the inversible tubular member.

In one possible implementation of the method, both the forming and inter-engaging of the stitches may be performed in a knitting process.

In another possible implementation of the method, a series of the stitches may be formed in the filamentary material and thereafter the stitches may be interengaged in a knitting process. The series of stitches may, for example, be formed as a series of loops in the filamentary material by forming the filamentary material into a helix and then flattening the helix.

The knitting process, where applicable, may be performed by means of a knitting spool.

Further features of the invention, in its various aspects, will become apparent from the description below of example embodiments of the invention, with reference to and as illustrated in the accompanying diagrammatic drawings. In the drawings.

In FIGS. 1 to 4, a first embodiment of a gripping device, in accordance with the invention, more particularly a laparoscopic surgical retrieval device, is designated generally by the reference numeral 10.

The retrieval device 10 includes:
an outer tubular member 12 defining a distal end 14, a proximal end 16, and a longitudinal passage 17 extending from the distal end 14 to the proximal end 16;
a first hand grip formation 18 around the proximal end 16 of the outer tubular member 12;
an elongate inner member in the form of an inner tubular member 20 defining a distal end 22, a proximal end 24, and a longitudinal passage 25 extending from the distal end 22 to the proximal end 24, the inner tubular member 20 being snugly and slidingly received through the passage 17 of the outer tubular member 12;
a second hand grip formation 26 on the proximal end 24 of the inner tubular member 20; and
a tubular member 27.

The tubular member 27 comprises:
a first length 29.1, secured around the distal end 14 of the outer tubular member 12;
a second length 29.2, secured around the distal end 22 of the inner tubular member 20; and
a third length 28, which is an inversible tubular member, in accordance with the invention, and which extends from the length 29.1 to the length 29.2.

The entire tubular member 27 was formed as an inversible tubular member, in accordance with the invention. However, the lengths 29.1 and 29.2 of the tubular member 27 clearly are now restrained and therefore no longer inversible.

The inversible tubular member 28 has:
an everted end 30, secured to the distal end 14 of the outer tubular member 12 via the first length 29.1; and
an opposite, inverted end 32, secured to the distal end 22 of the inner tubular member 20 via the second length 29.2.

Figure 4:
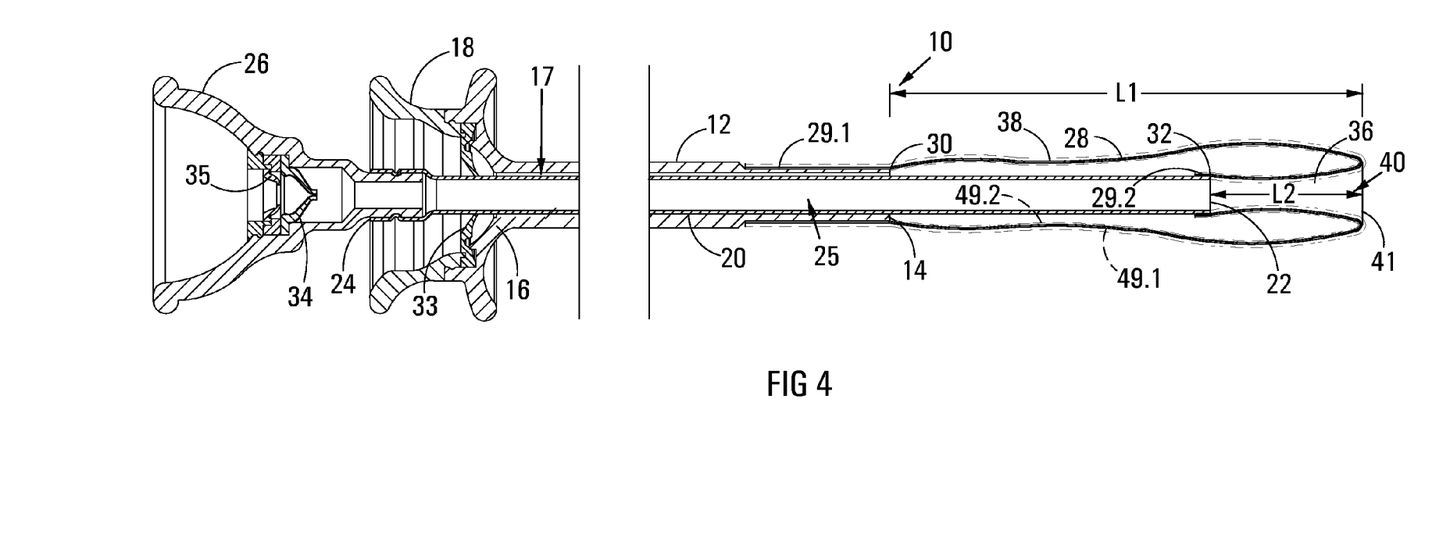
FIG. 4 shows a broken long section of the device of FIG. 1.

It is known that in certain laparoscopic procedures, it is required for a surgical retrieval device to seal up to a particular pressure, being a pressure maintained inside a peritoneal cavity during surgery. Accordingly, the retrieval device 10 includes a seal 33 effectively sealing between the inner tubular member 20 and the outer tubular member 12. The seal 33 seals up to a prescribed pressure, which is not less than 15 mmHg. Alternatively, the inner tubular member 20 may be received sufficiently snugly within the outer tubular member 12 to seal to a prescribed pressure, which is not less than 15 mmHg.

The passage 25 extends also through the hand grip formation 26. The retrieval device 10 includes also, within a widened proximal end of the passage 25, sealing means in the form of a circular seal 35 and a duckbill 34, both capable of sealing up to at least 15 mmHg. Another surgical device may be inserted through the retrieval device 10, particularly through the circular seal 35, the duckbill 34, and the passage 25. The circular seal 35 is for sealing around such a surgical device. The duckbill 34 is for sealing when there is no such surgical device present.

A length 38 of the inversible tubular member 28, having a length L1, is in an everted condition and a length 36 of the inversible tubular member 28, having a length L2, is in an everted condition. The inverted length 36 defines therein a cavity 40 which forms an extension of the passage 25. At a peripheral boundary between the inverted length 36 and the everted length 38 is defined a transformation end 41 of the inversible tubular member 28. As will be described below, the gripping device 10 is operable to effect progressive inversion and eversion of the inversible tubular member 28 at the transformation end 41, meaning that L1 and L2 are variable.

The inversible tubular member 28 has a total length L=L1+L2 of about six times a natural or relaxed outer diameter of the inverted length 36. The diameter of the inversible tubular member 28 may be variable along its length when it is entirely everted. In an alternative embodiment (not shown), the diameter of the inversible tubular member may be at least substantially constant along its length when it is entirely everted.

With the inversible tubular member 28 completely everted (not shown), then by relative forward displacement of the hand grip formation 18 and the outer tubular member 12 with respect to the hand grip formation 26 and the inner tubular member 20, the end 30 of the inversible tubular member 28 is linearly relatively displaced towards the transformation end 41 and the inversible tubular member 28 is progressively inverted, i.e. the inverted length 36 and the space or cavity 40 defined therein are progressively extended away from the distal end 22 of the inner tubular member 20. The everted length 38 clearly must have sufficient rigidity to cause such inversion.

Figure 5:
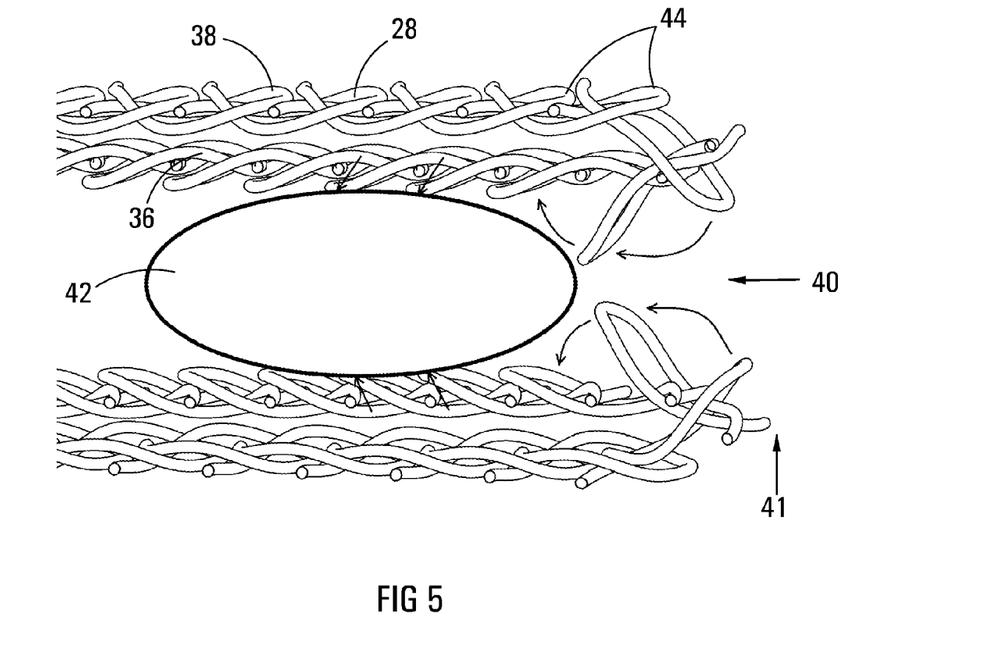
FIG. 5 shows a detail long section of an end part of the device of FIG. 1 and an object gripped thereby.

With reference particularly to FIG. 5, by such inversion, an object 42 can be gripped by means of the inversible tubular member 28 and drawn into the cavity 40. FIG. 5 will be referred to again below.

With the inversible tubular member 28 completely inverted (not shown) within the outer tubular member 12, then by relative rearward displacement of the hand grip formation 18 and outer tubular member 12 with respect to the hand grip formation 26 and the inner tubular member 20, the end 32 of the inversible tubular member 28 is linearly relatively displaced towards the transformation end 41 and the inversible tubular member 28 is progressively everted, i.e. the inverted length 36 and the space or cavity 40 defined therein are progressively shortened. The inverted length 36 clearly must have sufficient rigidity to cause such eversion.

Figure 6:
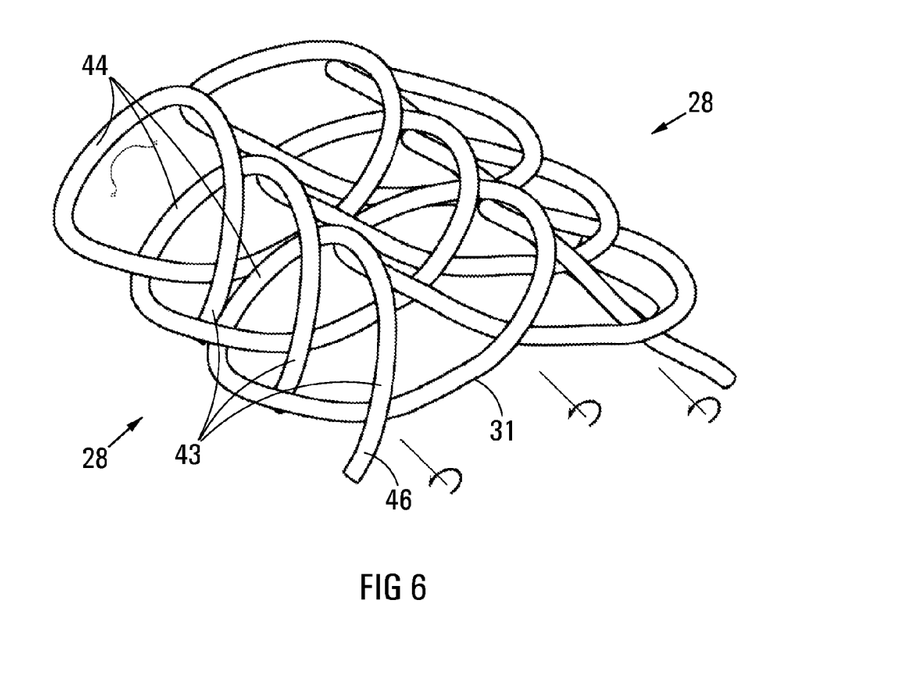
FIG. 6 shows a detail of an inverted length of the inversible tubular member of FIG. 1.

With reference now to FIG. 6, the inversible tubular member 28 (of which only a small portion is shown) is composed of interengaged plait stitches 43, each including a loop 44, the stitches 43 being made of a resiliently flexible filamentary material in the form of nylon filament 46. The same applies to the entire tubular member 27, of which the inversible tubular member 28 forms a part.

The loops 44 may be formed and interengaged in a knitting process, for example using a knitting spool. Alternatively, a series of the loops 44 may be formed in the nylon filament 46 prior to interengaging the loops in a knitting or similar process. This may be done by forming the filament 46 into a helix and then flattening the helix.

Figure 7:
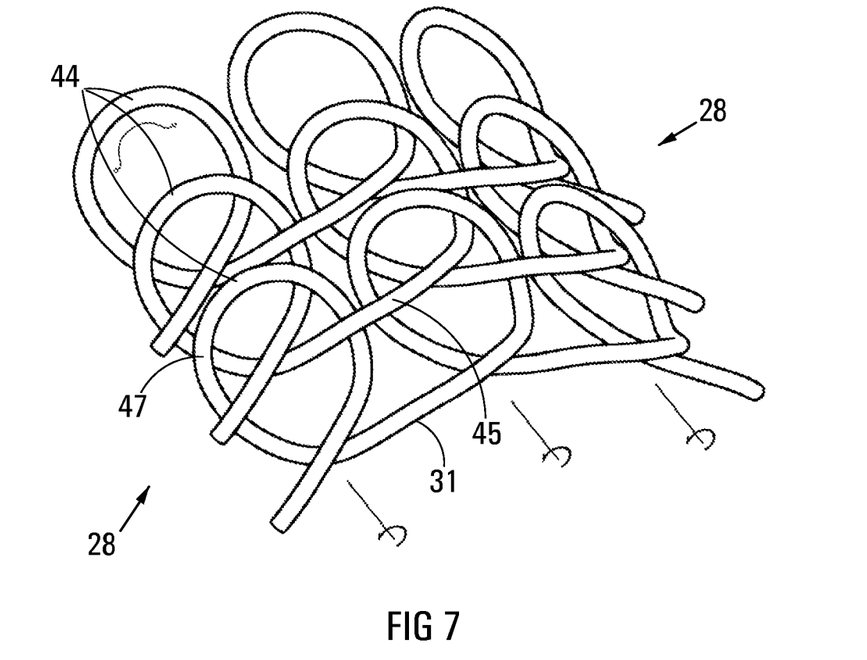
FIG. 7 shows a detail of an everted length of the inversible tubular member of FIG. 1.

FIG. 6 shows the portion of the inversible tubular member 28 in the inverted condition. FIG. 7 shows essentially the same portion of the inversible tubular member 28 in the everted condition.

Figure 8:
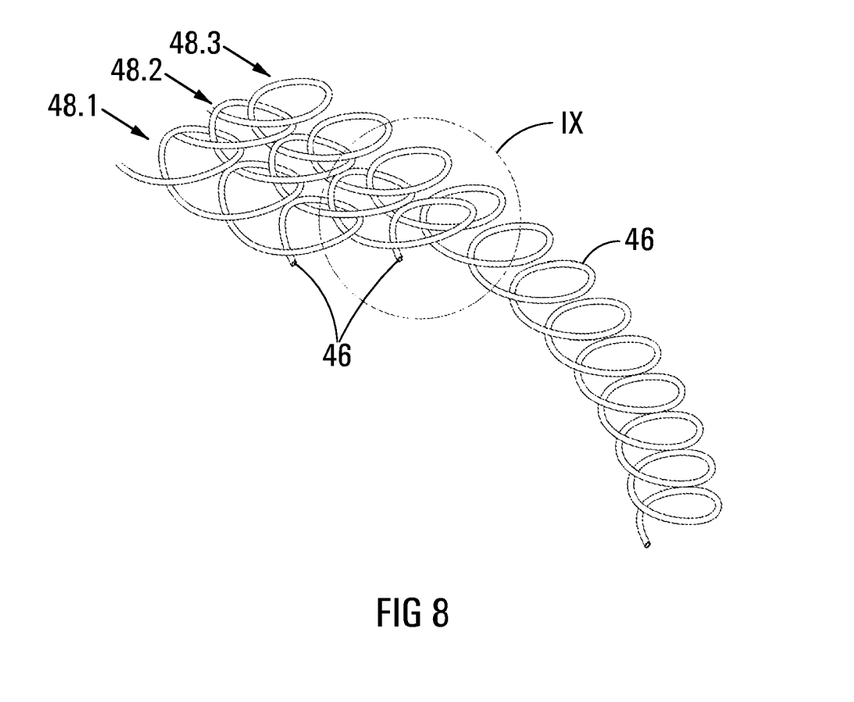
FIG. 8 shows a detail illustrating a step in a method, in accordance with the invention, of making the inversible tubular member of FIG. 1.
Figure 9:
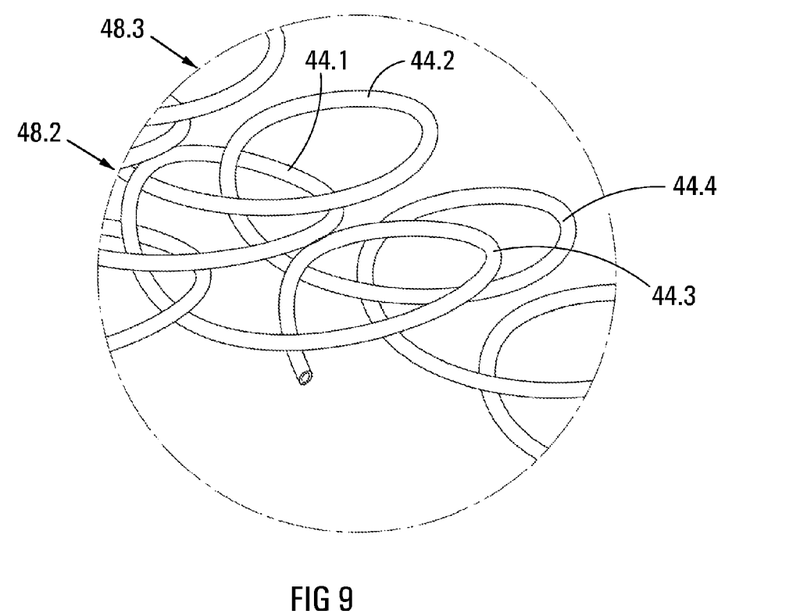
FIG. 9 shows a detail IX of FIG. 8.

FIGS. 8 and 9 show a step in a method, in accordance with the invention, for making the inversible tubular member 28. The nylon filament 46 is knitted such as to form circumferential rows, of which three rows 48.1, 48.2, and 48.3 are shown, in a helix pattern. In this case, the rows 48.1 and 48.2 have already been completed and the row 48.3 is being formed. Two loops 44.1 and 44.2 respectively in the rows 48.2 and 48.3 have been interengaged and two loops 44.3 and 44.4 in the respective rows are about to be interengaged. Such stitches are known in relation to, for example, yarn as plaited stitches and therefore do not require further elaboration herein.

At the time of making the inversible tubular member 28, the loops 44 are in the arrangement shown in FIG. 6, the loops 44 being on the inside of the inversible tubular member 28. This arrangement corresponds to the inverted condition of the inversible tubular member 28, as referred to herein. This arrangement is referred to below as the "inner loop arrangement".

By everting the inversible tubular member 28 into its everted condition, the loops 44 are transformed into the arrangement shown in FIG. 7, in which the loops 44 are on the outside of the inversible tubular member 28. This arrangement is referred to below as the "outer loop arrangement".

The inventor has found in practice that an inversible tubular member such as the inversible tubular member 28 naturally defines in its inverted condition an outer diameter which is smaller than its outer diameter in the everted condition. The bias created in the knitting process as the loops 44 are formed causes adjacent loops to overlap in the inverted condition while they are constrained to a side-by-side arrangement in the everted condition. This creates two stable diameters respectively for the inversible tubular member 28 in the inverted and everted conditions, meaning that there is very low friction and minimal interference between the inverted length 36 and the everted length 38 (see FIG. 4).

A possible further explanation of the two diameters is given below:

All of the loops 44, having been constructed as a helical spring either during or before the knitting process, have a tendency to want to return to a stacked, helical arrangement. This results in two forces on the loops:

A force pulling the loops 44 together due to the fact that the apex of the loop is highly flexed and creates a tendency for the loop to attempt to decrease its rate of flexure. As the loop is attached to its neighbouring loops by the roots 31 this effect pulls neighbouring loops together as each attempts to expand; and A moment around the axis of symmetry of each loop 44 which attempts to return the loops to a parallel arrangement.

In the inner loop arrangement, the root 31 between loops in the next row passes on the inside of the curvature and the loops 44 are therefore not fully constrained in rotation and are able to rotate slightly about their axes. This rotation also allows them to overlap with the loops 44 to either side. As the loops 44 are not restricted from circumferential overlap, the force created by the highly flexed apex of the loops 44 is able to pull the loops 44 together and they partially overlap each other which results in a smaller circumference and, thus results in a smaller diameter.

In the outer arrangement the loops 44 are unable to rotate due to the root 31 of the next row now passing over the loops 44 and following the increased path of the outside of the curvature. This creates an inward force on the loops 44 and they are restricted from rotation and circumferential overlap (at 45 in FIG. 7). The moment about their axes further tensions the roots and the side-by-side arrangement now creates a greater circumference and, thus results in a greater diameter.

The loops in the outer loop arrangement are also restricted from longitudinal overlap (at 47 in FIG. 7), which increases the longitudinal stiffness and rigidity of the everted length of the inversible tubular member and provides the rigidity required for the everted length to withstand the forces of inversion and ingesting a captured object without crumpling and without the need for alternative support.

Figure 1:
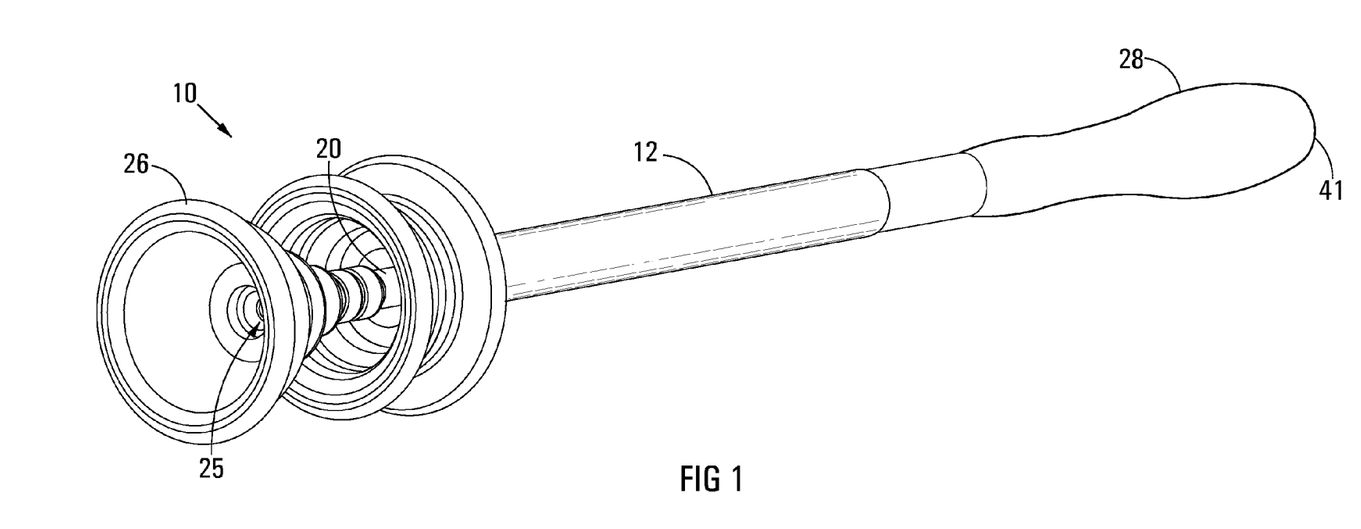
FIG. 1 shows a side/rear three-dimensional view of a first embodiment of a gripping device, in accordance with the invention, including an inversible tubular member, in accordance with the invention.
Figure 2:
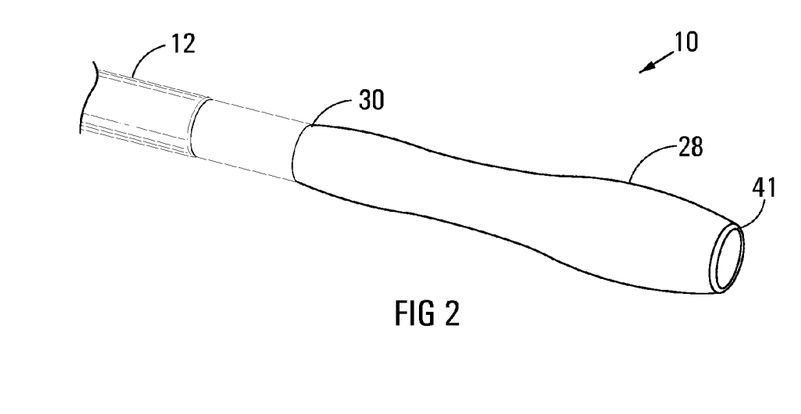
FIG. 2 shows an enlarged side/front three-dimensional view of a distal end portion of the device of FIG. 1.
Figure 3:
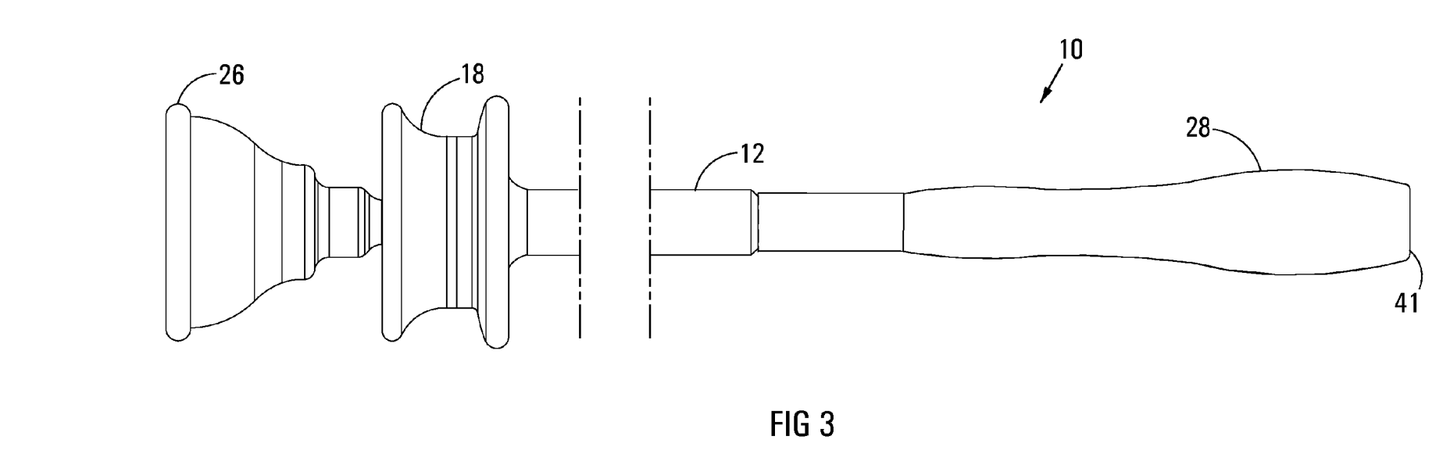
FIG. 3 shows a broken side view of the device of FIG. 1.

Referring now particularly to FIGS. 1 and 5, in order to use the retrieval device 10 for gripping the object 42, say during a laparoscopic procedure on a person, the hand grip formations 18 and 26 are pushed together until substantially the entire inversible tubular member 28 is in the everted condition as an extension to the outer tubular member 12. The inversible tubular member 28 and outer tubular member 12 is then at least partially inserted into the body through a standard laparoscopic port. The object 42 is contacted by the transformation end 41 of the inversible tubular member 28. The hand grip formations 18 and 26 are progressively pulled apart so that the inversible tubular member 28 grips the object 42 and draws it into the cavity 40. This is an example of the method of the third aspect of the invention.

In the inversible tubular member 28, the loops 44 on the outside of the everted length 38 point in the distal direction. As the loops 44 approach the transformation end 41 during inversion, they do not project past the outer diameter of the inversible tubular member 28. As they pass the end 41, they project inwardly into the cavity 40 and proximally for a short travel distance. This behavior of the loops 44 enhances grip of the loops 44 on the object 42.

The applicant has found with the prototype of the retrieval device 10 that the inversible tubular member 28 will stretch sufficiently for ingesting a sphere of a diameter of 1.5 times the average relaxed outer diameter of the inverted length 36. Take a case where the inversible tubular member 28 is halfway inverted when the sphere is halfway into the inversible tubular member 28 at the transformation end 41. In this case, the applicant has found that further inversion occurs at the transformation end 41.

Optionally, a membrane 49.1 (shown in broken lines in FIG. 4) may be applied over the surface of the inversible tubular member 28 which is an outer surface in the everted condition. Alternatively or additionally, such a membrane 49.2 may be applied over the opposite surface. Such a membrane may, for example, serve to prevent spillage of toxins from tissue removed during a surgical procedure.

As was stated above, the diameter of the inversible tubular member 28 may be variable along its length when it is entirely everted. This may be achieved by varying the sizes of the loops, or the number of loops per row, along the length of the inversible tubular member. Alternatively, if the properties of the filamentary material permit, a variable diameter may be achieved by heating, setting, and cooling of the material.

Figure 10:
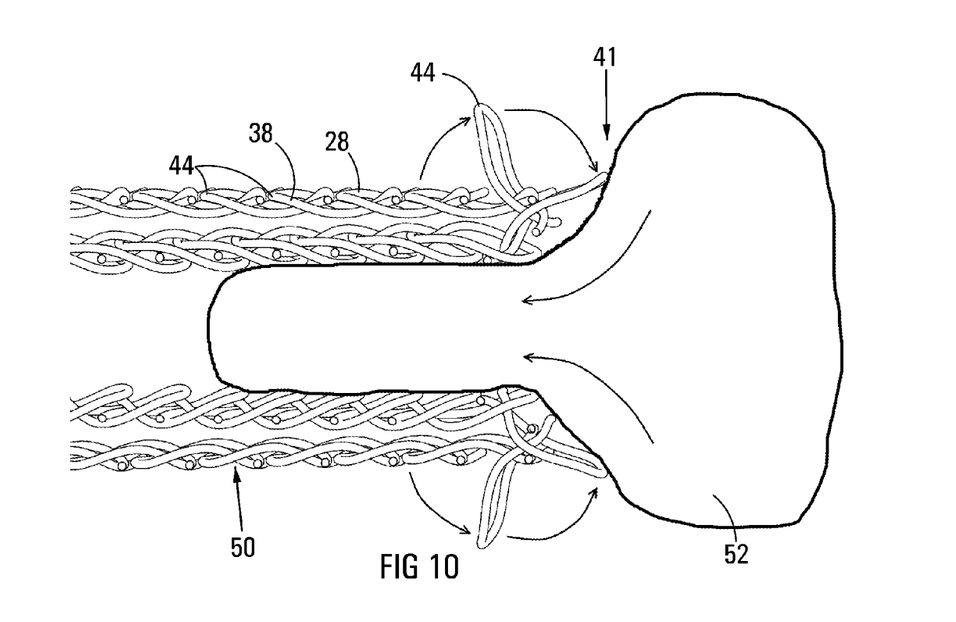
FIG. 10 shows a detail long section of an end part of a second embodiment of a gripping device, in accordance with the invention, and an object gripped thereby, the device being for the most part identical to the gripping device of FIG. 1.

In FIG. 10, a second embodiment of a gripping device in the form of a laparoscopic surgical retrieval device, in accordance with the invention, of which only a part is shown, is designated generally by the reference numeral 50.

The retrieval device 50 is for the most part identical to the retrieval device 10 of FIGS. 1 to 9 and therefore like features, where shown, will again be designated by the same reference numerals as before and these features will not be described again. Moreover, the retrieval device 50 differs from the retrieval device 10 only in respect of the orientation of its inversible tubular member 28. In this case, the loops 44 on the outside of the everted length 38 of the length of the inversible tubular member 28 point in the proximal direction.

As the loops 44 approach the transformation end 41 during inversion, they project past the outer diameter of the inversible tubular member 28. As they pass the transformation end 41, they do not project inwardly into the cavity 40. This behavior of the loops 44 means that the transformation end 41 can effectively gather material over an area larger than its outer diameter 28. This feature may also aid gripping and drawing in of an object 52 which tends to break apart.

Figures 11, 12, 13:
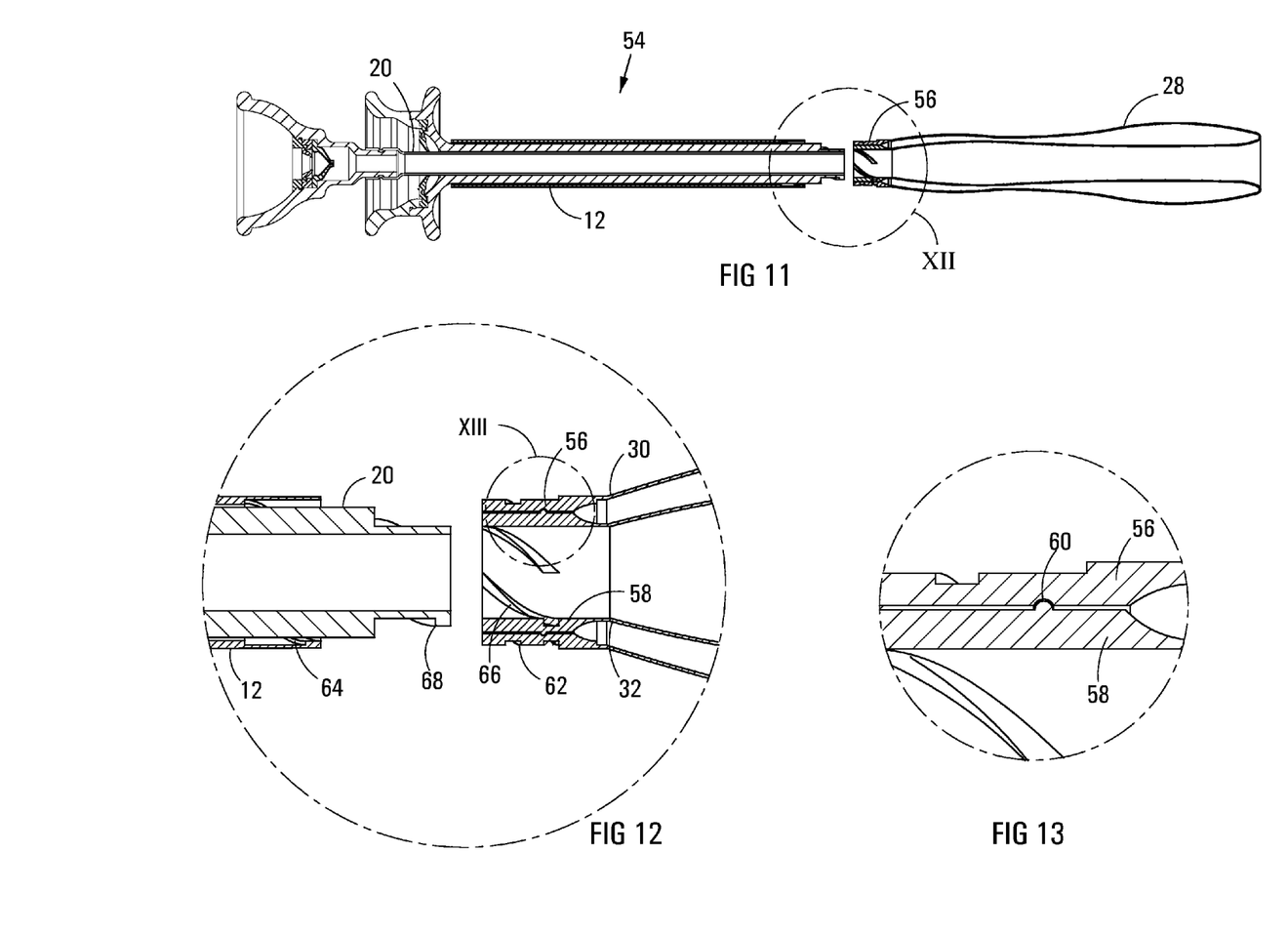
FIG. 11 shows a long section of a third embodiment of a gripping device, in accordance with the invention.
FIG. 12 shows a detail XII of FIG. 11.
FIG. 13 shows a detail XIII of FIG. 12.

In FIG. 11, a third embodiment of a gripping device in the form of a laparoscopic surgical retrieval device, in accordance with the invention, of which only a part is shown, is designated generally by the reference numeral 54.

The retrieval device 54 is for the most part identical to the retrieval device 10 of FIGS. 1 to 9 and therefore like features, where shown, will again be designated by the same reference numerals as before and these features will not be described again.

With reference to FIGS. 11 to 13 generally, the retrieval device 54 includes:
- a tubular first coupling 56 to which the everted end 30 of the inversible tubular member 28 is peripherally attached; and
- a tubular second coupling 58 to which the inverted end 32 of the inversible tubular member 28 is peripherally attached.

By relative axial displacement, the second coupling 58 fits into the first coupling 56 in a snug fit. These couplings define complementary clip-in formations 60 for retaining the coupling 58 in the coupling 56.

The coupling 56 defines an outer screw thread 62 complementary to an inner screw thread 64 defined by the distal end of the outer tubular member 12.

The coupling 58 defines an inner screw thread 66 complementary to an outer screw thread 68 defined by the distal end of the inner tubular member 20.

The extractor device 54 provides the following operation. With the couplings 56 and 58 engaged respectively with the tubular members 12 and 20 by screwing them in, the device 54 is used similarly to the use of the retrieval device 10 as described above to grip an object in a body of, say, a person. The tubular members 12 and 20 are relatively longitudinally displaced until the object is at least partially within the cavity 40 and the clip-in formations 60 are interengaged. The tubular members 12 and 20 are then unscrewed from the respective couplings 56 and 58, which may require the inversible tubular member 28 to be held by means of another surgical instrument.

The inversible tubular member 28 has a diameter which may vary substantially along its length to facilitate operative holding of an object received therein.

Figure 14:
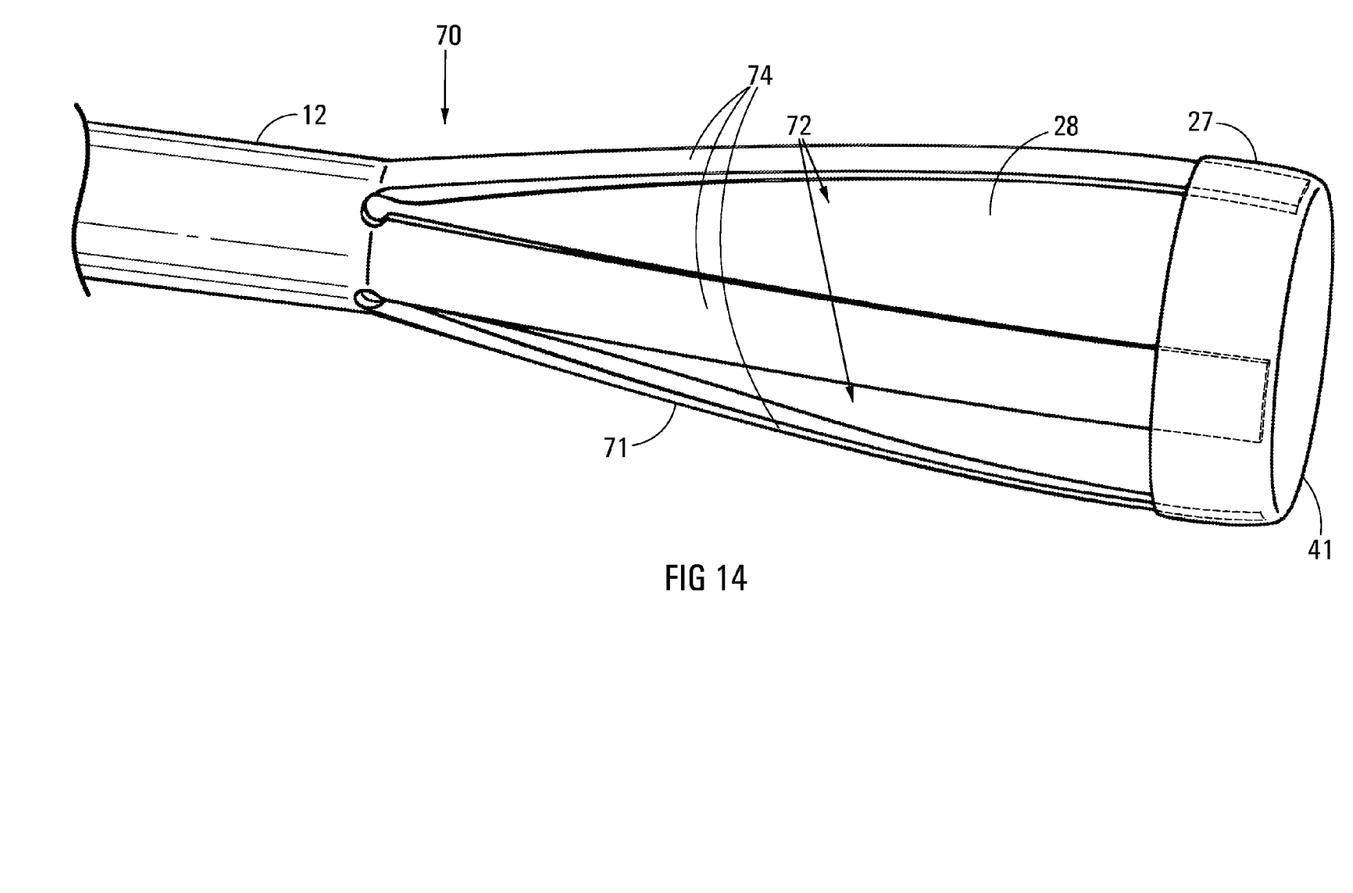
FIG. 14 shows a three-dimensional view of a fourth embodiment of a gripping device, in accordance with the invention, including an inversible tubular member, in accordance with the invention.

In FIG. 14, a fourth embodiment of a gripping device in the form of a laparoscopic surgical retrieval device, in accordance with the invention, of which only a part is shown, is designated generally by the reference numeral 70.

The retrieval device 70 is for the most part identical to the retrieval device 10 of FIGS. 1 to 9 and therefore like features, where shown, will again be designated by the same reference numerals as before and these features will not be described again.

An outer tubular member 12 of the retrieval device 70 is made of a resiliently flexible material, e.g. polypropylene. It includes an end portion 71 defining therein four elongate slits 72 (only two shown), angularly evenly spaced about its central axis. As such, the end portion 71 is split into four fingers 74 (only three shown). Distal ends of the fingers 74 have an everted end of a tubular member 27, which includes an inversible tubular member 28, secured to their outsides. An opposite end of the inversible tubular member 28 is secured to an inner tubular member (see reference numeral 20 in FIG. 4).

The inversible tubular member 28 is shown almost entirely in an inverted condition. The fingers 74 are shown resiliently deformed into a flared out or expanded condition and similarly, the inversible tubular member 28 is shown in a radially expanded condition. Such expansion will, in use of the retrieval device 70, be caused by an "oversized" ingested object (not shown) in the inversible tubular member 28.

It will be understood that, in an ex-factory condition of the retrieval device 70, the fingers 74 were more closely spaced and defined a circumference substantially the same as that of the remainder of the tubular member 12.

Other features and operation of the retrieval device 70 are essentially the same as those of the retrieval device 10 of FIGS. 1 to 9. Expansion of the end portion 71 merely facilitates ingestion of larger objects than would have been the case with the retrieval device 10.

In all of the above examples, the gripping device of the invention was intended for surgical use. It must be appreciated, however, that a similar gripping device may be configured for other uses, for example an industrial use. It may be suitably scaled up or down for a required application. For certain heavier duty applications, the resiliently flexible filamentary material may, for example, be a multifilament material, for example stranded stainless steel wiring or cabling.

It is envisaged that, generally in all practical embodiments of the gripping device of the invention, requirements a), b), and c) below will apply. The numbers in brackets refer to equivalent features of the retrieval device 10 of FIGS. 1 to 9.

a) With the inversible tubular member (28) at least partially inverted, the inverted length (36) must have sufficient stiffness to cause eversion of the inversible tubular member at the transformation end (41) upon axial displacement of the inverted end (32) towards the transformation end, for a length of the inverted length (L2) up to X times an average relaxed outer diameter of the inverted length, with X>=2.0. In some possible embodiments, X>=5.0.

b) With the inversible tubular member (28) at least partially everted, the everted length (38) must have sufficient stiffness to cause inversion of the inversible tubular member at the transformation end (41) upon axial displacement of the everted end (30) towards the transformation end, for a length (L1) of the everted length up to Y times an average relaxed outer diameter of the inverted length, with Y>=2.0. In some possible embodiments, Y>=5.0 c) With the inversible tubular member (28) at least partially everted, the everted length (38) must have sufficient stiffness to cause inversion of the inversible tubular member at the transformation end (41) upon axial displacement of the everted end (30) towards the transformation end, for a length (L1) of the everted length up to Z times the average relaxed outer diameter of the inverted length, whilst one half of a sphere of diameter 1.5 times an average relaxed outer diameter of the inverted length is received in the inversible tubular member at the transformation end, with Z>=2.0.

The invention claimed is:

1. An inversible tubular member, the inversible tubular member being substantially round in cross-section and progressively transformable between an everted condition and an inverted condition, with a transformation end being defined intermediate an everted length and an inverted length of the inversible tubular member during such transformation and with the inverted length and the everted length defining opposite to the transformation end respectively an inverted end and an everted end of the inversible tubular member,
wherein the inversible tubular member is composed of interengaged knitted stitches of resiliently flexible filamentary material;
wherein, with the inversible tubular member at least partially inverted, the inverted length has sufficient stiffness to cause eversion of the inversible tubular member at the transformation end upon axial displacement of the inverted end towards the transformation end, for a length of the inverted length up to X times an average relaxed outer diameter of the inverted length;
wherein X>=2.0;
wherein, with the inversible tubular member at least partially everted, the everted length has sufficient stiffness to cause inversion of the inversible tubular member at the transformation end upon axial displacement of the everted end towards the transformation end, for a length of the everted length up to Y times an average relaxed outer diameter of the inverted length;
wherein Y>=2.0;
wherein an outer diameter in the everted condition is larger than an outer diameter in the inverted condition, and an inner diameter in the everted condition is larger than an outer diameter in the inverted condition;
wherein the stitches are of at least one length of the filamentary material, the stitches are plaited stitches, and the stitches each define a loop and are knitted to form circumferential rows arranged in a helix pattern;
wherein each stitch includes a loop, the loops of the inverted length being on the inside of the inversible tubular member and the loops of the everted length being on the outside of the inversible tubular member; and
wherein each loop is connected to the loop of an adjacent stitch by a root, the roots of the stitches of the everted length being positioned on the outside of the loops of the stitches of an adjacent row of stitches and the roots of the stitches of the inverted length being positioned on the inside of the loops of the stitches of an adjacent row of stitches.

2. An inversible tubular member as claimed in claim 1, wherein:
with the inversible tubular member at least partially everted, the everted length has sufficient stiffness to cause inversion of the inversible tubular member at the transformation end upon axial displacement of the everted end towards the transformation end, for a length of the everted length up to Z times the average relaxed outer diameter of the inverted length, whilst one half of a sphere of diameter 1.5 times an average relaxed outer diameter of the inverted length is received in the inversible tubular member at the transformation end; and $$Z>=2.0.$$

3. An inversible tubular member as claimed in claim 1, wherein the filamentary material is a monofilament material.

4. An inversible tubular member as claimed in claim 1, wherein the filamentary material is a multifilament material.

5. An inversible tubular member as claimed in claim 1, wherein the filamentary material is a superelastic material.

6. An inversible tubular member as claimed in claim 1, wherein the filamentary material is a shape memory material.

7. An inversible tubular member as claimed in claim 1, further comprising a variable diameter along its length in each of the inverted and everted conditions.

8. A gripping device, comprising:
the inversible tubular member of claim 1; and
actuation means carrying the inversible tubular member and operable for effecting progressive inversion and eversion of the inversible tubular member at the transformation end, with such inversion providing for gripping an object in the inversible tubular member, wherein the actuation means comprises:
an outer tubular member defining a distal end, and a proximal end, and a longitudinal passage extending between the distal end and the proximal end, the distal end being peripherally attached to an everted end of the inversible tubular member,
an inner elongate member received within the passage and defining a distal end and a proximal end, the distal end being peripherally attached to an opposite inverted end of the inversible tubular member, the outer tubular member and the inner elongate member being slidingly displaceable relative to each other to effect the progressive inversion and eversion,
a first hand grip formation on the proximal end of the outer tubular member, and
a second hand grip formation on the proximal end of the inner elongate member,
the hand grip formations being manually relatively displaceable for effecting the relative sliding displacement of the outer tubular member and the inner elongate member.

9. A gripping device as claimed in claim 8, further comprising sealing means sealing between the inner elongate member and the outer tubular member to a required pressure, which is not less than 15 mmHg.

10. A gripping device as claimed in claim 9, wherein the inner elongate member defines therethrough a longitudinal passage, permitting insertion of an elongate surgical or other instrument through it, in which the inner elongate member has sealing means sealing the longitudinal passage defined therethrough, the sealing means being configured to permit passage of the elongate surgical or other instrument through it and to seal around the instrument.

11. A gripping device as claimed in claim 8, wherein the inversible tubular member is releasable from the outer tubular member and the inner elongate member, the gripping device including:
   a first coupling secured to the everted end of the inversible tubular member, the first coupling being releasably engageable with the distal end of the outer tubular member; and
   a second coupling secured to an end of the inverted length of the inversible tubular member opposite to the transformation end, the second coupling being releasably engageable with the distal end of the inner tubular member, the first and second couplings being interengageable through relative displacement of the outer tubular member and the inner elongate member.

12. A gripping device as claimed in claim 8, wherein the distal end of the outer tubular member includes a distal end portion that is radially expandable for operatively accommodating therein a length of the inversible tubular member and an object therein where the size of the object requires radial expansion of the distal end portion, wherein the distal end portion defines therein an arrangement of resiliently flexible slits which are angularly spaced about the central axis of the outer tubular member to provide for the expansion.

13. A method of gripping an object, the method including:
   providing the inversible tubular member of claim 1;
   with at least a part of the inversible tubular member in the everted condition, contacting the transformation end of the part with the object; and
   progressively inverting the part at the transformation end, thus causing the inversible tubular member to grip the object.

* * * * *